(12) United States Patent
Macfie et al.

(10) Patent No.: US 8,940,141 B2
(45) Date of Patent: Jan. 27, 2015

(54) ANALYTICAL TEST STRIP WITH AN ELECTRODE HAVING ELECTROCHEMICALLY ACTIVE AND INERT AREAS OF A PREDETERMINED SIZE AND DISTRIBUTION

(75) Inventors: Gavin Macfie, Culloden Moor (GB); Craig Redpath, Culloden Moor (GB); James Iain Rodgers, Lochardil (GB); Neil Whitehead, Dingwall (GB)

(73) Assignee: Lifescan Scotland Limited, Inverness (GB)

( * ) Notice: Subject to any disclaimer, the term of this patent is extended or adjusted under 35 U.S.C. 154(b) by 744 days.

(21) Appl. No.: 12/783,437

(22) Filed: May 19, 2010

(65) Prior Publication Data
US 2011/0284393 A1 Nov. 24, 2011

(51) Int. Cl.
*C12M 1/00* (2006.01)
*G01N 27/26* (2006.01)
*G01N 33/487* (2006.01)
*G01N 27/327* (2006.01)

(52) U.S. Cl.
CPC .................................. *G01N 27/3272* (2013.01)
USPC ................... 204/403.01; 204/403.04; 205/792

(58) Field of Classification Search
USPC ................ 204/400, 403.01–403.15; 205/775, 205/777.5, 792
See application file for complete search history.

(56) References Cited

U.S. PATENT DOCUMENTS

| | | | |
|---|---|---|---|
| 6,110,354 A | 8/2000 | Saban et al. | |
| 6,241,862 B1 | 6/2001 | McAleer et al. | |
| 6,662,439 B1 | 12/2003 | Bhullar | |
| 6,733,655 B1 | 5/2004 | Davies et al. | |
| 7,073,246 B2 | 7/2006 | Bhullar et al. | |
| 7,386,937 B2 | 6/2008 | Bhullar et al. | |
| 7,476,827 B1 | 1/2009 | Bhullar et al. | |

(Continued)

FOREIGN PATENT DOCUMENTS

| | | |
|---|---|---|
| CN | 1839313 A | 9/2006 |
| CN | 1902480 A | 1/2007 |

(Continued)

OTHER PUBLICATIONS

Amatore, Christian, "Theory and Experiments of Transport at Channel Microband Electrodes Under Laminar Flow. 3. Electrochemical Detection at Electrode Arrays under Steady State," Analytical Chemistry, vol. 82, No. 6, Mar. 15, 2010, pp. 2434-2440.

(Continued)

*Primary Examiner* — Luan Van
*Assistant Examiner* — Maris R Kessel

(57) ABSTRACT

An electrochemical-based analytical test strip for the determination of an analyte (e.g., glucose) in a bodily fluid sample (such as a whole blood sample) includes an electrically insulating base layer and a patterned conductor layer (for example, a gold patterned conductor layer) disposed over the electrically-insulating layer. The patterned conductor layer includes at least one electrode with the electrode having electrochemically inert areas and an electrochemically active area(s). Moreover, the electrochemically inert areas and electrochemically active area(s) are of a predetermined size and a predetermined distribution such that electrochemical response of the electrode during use of the electrochemical-based analytical test strip is essentially equivalent to a predetermined electrochemical response.

30 Claims, 10 Drawing Sheets

(56) References Cited

U.S. PATENT DOCUMENTS

| | | |
|---|---|---|
| 2003/0175946 A1 | 9/2003 | Tokunaga et al. |
| 2004/0031682 A1 | 2/2004 | Wilsey |
| 2004/0040868 A1 | 3/2004 | DeNuzzio et al. |
| 2005/0023152 A1 | 2/2005 | Surridge et al. |
| 2005/0109618 A1 | 5/2005 | Davies |
| 2006/0144704 A1 | 7/2006 | Ghesquiere et al. |
| 2007/0227907 A1 | 10/2007 | Shah et al. |
| 2007/0240986 A1 | 10/2007 | Reymond et al. |
| 2009/0178935 A1 | 7/2009 | Reymond et al. |
| 2009/0310743 A1 | 12/2009 | Carpenter et al. |

FOREIGN PATENT DOCUMENTS

| | | |
|---|---|---|
| WO | 2004113910 A1 | 12/2004 |
| WO | WO 2005/045414 A1 | 5/2005 |
| WO | 2006072089 A1 | 7/2006 |
| WO | 2007114943 A2 | 10/2007 |
| WO | 2007120552 A2 | 10/2007 |
| WO | WO 2008-040982 A1 | 4/2008 |

OTHER PUBLICATIONS

Trevor J. Davies, et al: "Voltammetry at spatially heterogeneous electrodes", Journal of Solid State Electrochemistry; Current Research and Development in Science and Technology, Springer, Berlin, DE, vol. 9, No. 12, Dec. 1, 2005, pp. 797-808, XP019352548, ISSN: 1433-0768.

International PCT Search Report, PCT Application No. PCT/GB2011/000766, dated Aug. 16, 2011, 4 pages European Patent Office, Rijswijk, Netherlands.

Arrigan, Damien W. M., "Nanoelectrodes, nanoelectrode arrays and their applications", The Analyst, vol. 129, No. 12, Nov. 9, 2004, pp. 1157-1165.

European Search Report issued in related European Patent application No. 13171920.5, Sep. 10, 2013, 11 pages.

First Office Action issued in related Chinese Patent Application No. 201180024795.4, dated Nov. 29, 2013, 4 pages.

International Preliminary Report on Patentability issued in related International Application No. PCT/GB2011/000766, Dec. 13, 2012, 13 pages.

Scheller F. et al., "Gesetzmassigkeit fur den Diffusionsgrenzstrom an teilweise blockierten Modellelektroden", Journal of Electroanalytical Chemistry and Interfacial Electro Chemistry, Elsevier, Amsterdam, NL, vol. 19, No. 3, Nov. 1, 1968, pp. 187-198.

Search Report issued in related Chinese Patent Application No. 201180024795.4, dated Nov. 11, 2013, 2 pages.

Written Opinion issued in related International Application No. PCT/GB20111000766, Jul. 13, 2012, 4 pages.

Written Opinion issued in related International Application No. PCT/GB2011/000766, Nov. 16, 2012, 5 pages.

US 8,940,141 B2

ANALYTICAL TEST STRIP WITH AN ELECTRODE HAVING ELECTROCHEMICALLY ACTIVE AND INERT AREAS OF A PREDETERMINED SIZE AND DISTRIBUTION

BACKGROUND OF THE INVENTION

1. Field of the Invention

The present invention relates, in general, to medical devices and, in particular, to analytical test strips, associated meters and related methods.

2. Description of Related Art

The determination (e.g., detection and/or concentration measurement) of an analyte in a bodily fluid sample is of particular interest in the medical field. For example, it can be desirable to determine glucose, ketones, cholesterol, acetaminophen and/or HbA1c concentrations in a sample of a bodily fluid such as urine, blood or interstitial fluid. Such determinations can be achieved using analytical test strips, based on, for example, visual, photometric or electrochemical techniques. Conventional electrochemical-based analytical test strips are described in, for example, U.S. Pat. Nos. 5,708,247, and 6,284,125, each of which is hereby incorporated in full by reference.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention, in which.

DETAILED DESCRIPTION OF ILLUSTRATIVE EMBODIMENTS

Figure 1:
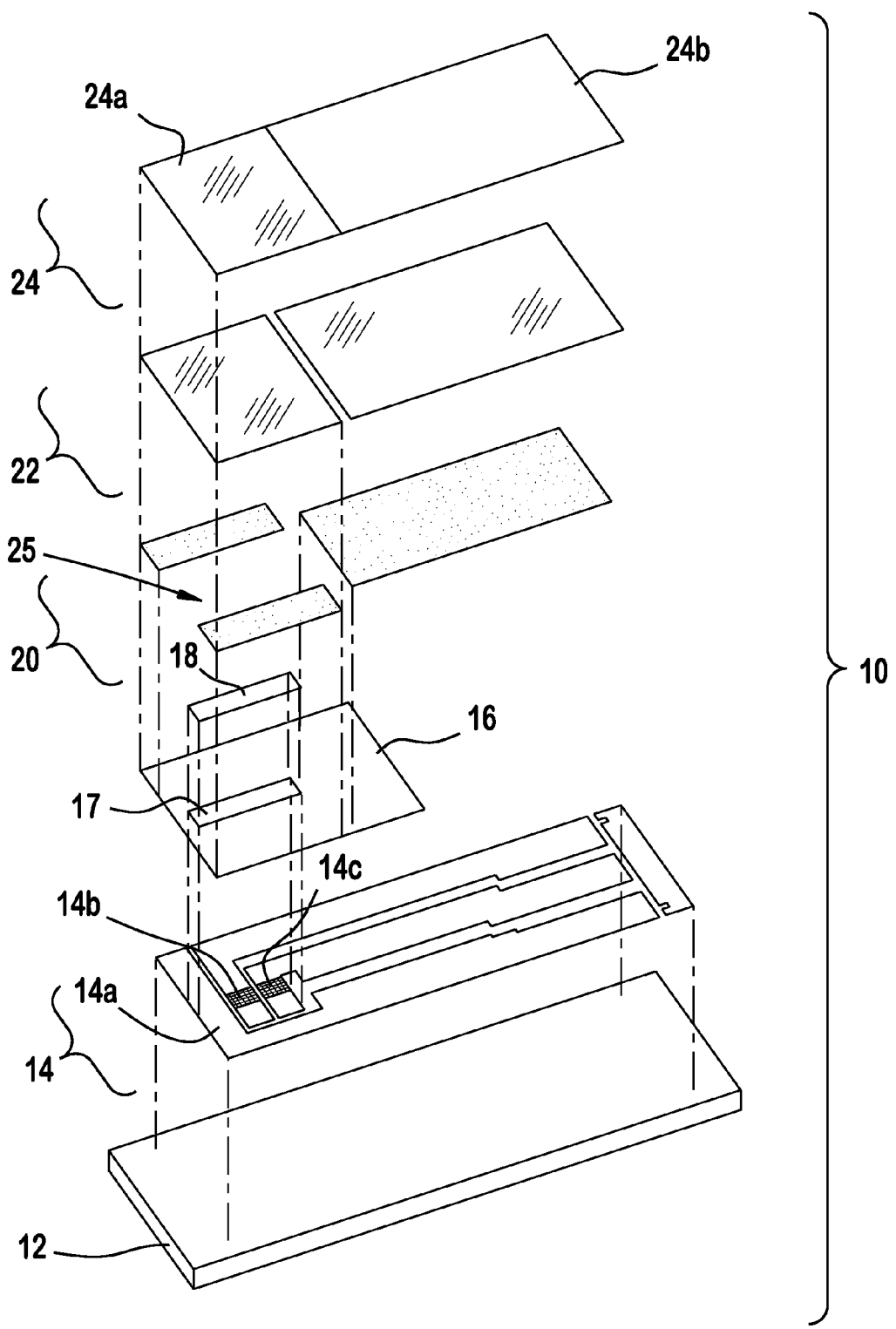
FIG. 1 is a simplified exploded view of an electrochemical-based analytical test strip according to an embodiment of the present invention with dashed lines indicating alignment of various elements of the electrochemical-based analytical test strip.

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein.

In general, an electrochemical-based analytical test strip for the determination of an analyte (e.g., glucose) in a bodily fluid sample (such as a whole blood sample) according to embodiments of the present invention includes an electrically insulating base layer and a patterned conductor layer (for example, a gold patterned conductor layer) disposed over the electrically-insulating layer. The patterned conductor layer includes at least one electrode with the electrode having at least one electrochemically inert area and electrochemically active areas. Moreover, the electrochemically inert area(s) and electrochemically active areas are of a predetermined size and a predetermined distribution (such as a regular lattice or regular array distribution) such that electrochemical response of the electrode during use of the electrochemical-based analytical test strip is essentially equivalent to a predetermined electrochemical response.

It should be noted that an electrode surface that includes both electrochemically active and electrochemically inert areas is referred to as an electrochemically heterogeneous electrode. Electrodes employed in embodiments of the present invention are unobvious and novel in that, for example, their electrochemically heterogeneous characteristics are predetermined via the size and distribution of the electrochemically active and inert areas such that a predetermined electrochemical response (e.g., peak current, separation current, transient response, early transient response within 500 milliseconds of the application of a potential to the electrochemical-based analytical test strip, and/or interferent electrochemical response) is obtained during use.

Electrochemical-based analytical test strips according to the present invention are beneficial in that, for example, the test strip electrode can be "tuned" (i.e., modified or adjusted in comparison to an electrode wherein the size and distribution of electrochemically inert and electrochemically active areas are not predetermined or controlled) to provide desirable predetermined electrochemical responses. Such tuning is achieved by the selection of an appropriate predetermined size and predetermined distribution of the electrochemically active and electrochemically inert areas. Once apprised of the present disclosure, one skilled in the art will recognize that such selection can be based on routine experimentation and modeling (e.g., mathematical modeling based on experimental results obtained across a range of predetermined sizes and distributions), the use of voltammetric sizing techniques as described herein, or any other suitable technique known to one skilled in the art.

A non-limiting example of an electrochemical-based analytical test strip according to the present invention is an electrochemical-based analytical test strip with a gold working electrode that has a predetermined size and distribution of electrochemically active and electrochemically inert areas that provides an electrochemical response essentially equivalent to a conventional screen-printed carbon working electrode. It is envisioned that such an electrochemical-based analytical test strip could be employed with an established base of meters employing analyte determination algorithms designed for analytical test strips with screen printed carbon working electrodes and, therefore, would not require the expense and effort of a new meter. In other words, electrochemical-based analytical test strips according to embodiments of the present invention can be, if desired, backward compatible with established meters. Moreover, the use of gold for the working electrode is anticipated to provide increased accuracy and reproducibility due to the inherent electrochemical efficiency reproducibility of gold electrodes.

Figure 2:
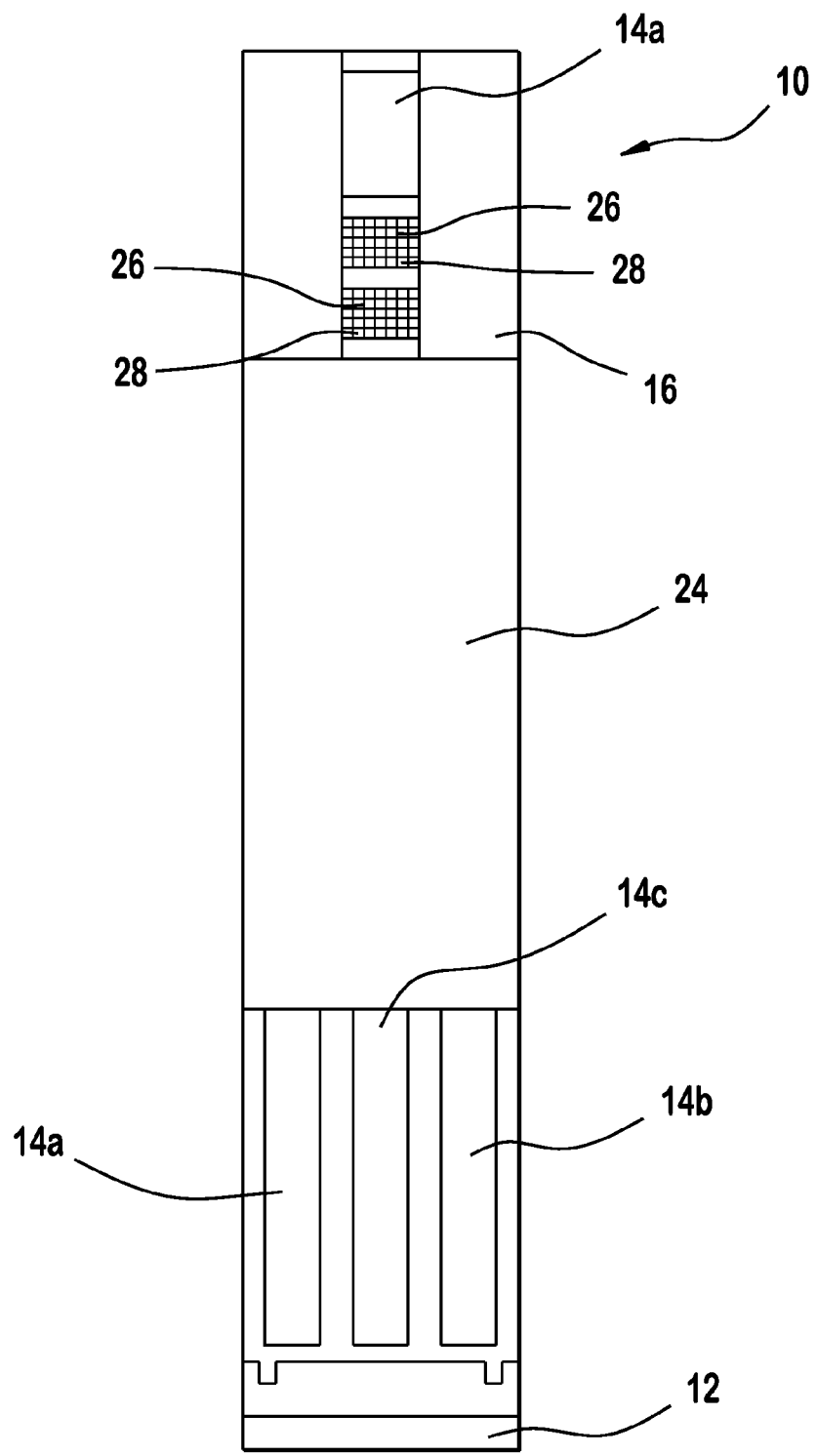
FIG. 2 is a simplified top view of the electrochemical-based analytical test strip of FIG. 1.
Figure 3:
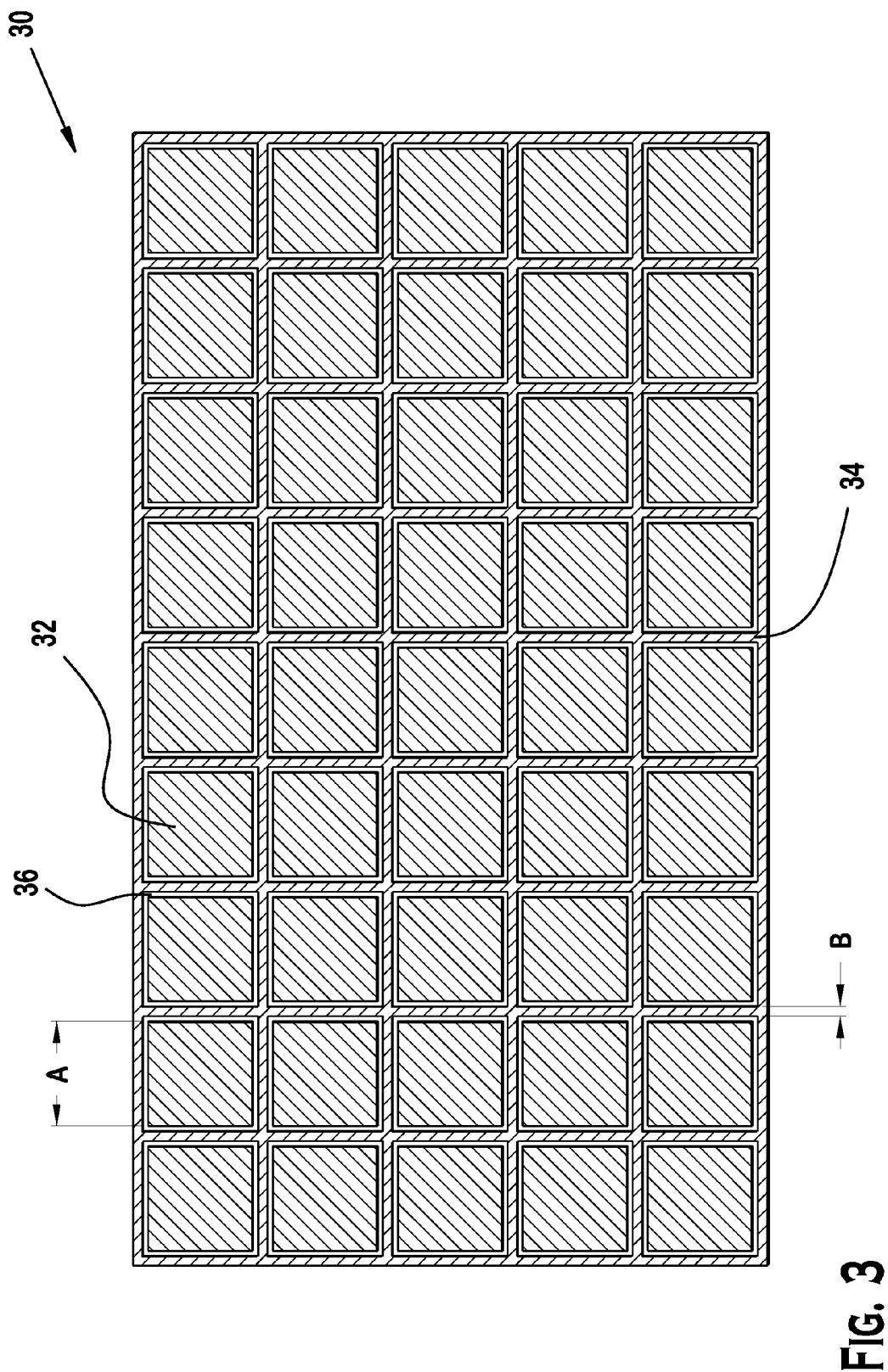
FIG. 3 is a simplified depiction of a regular square lattice array of electrochemically active areas and electrochemically inert areas of an electrode as can be employed in embodiments of the present invention.
Figure 4:
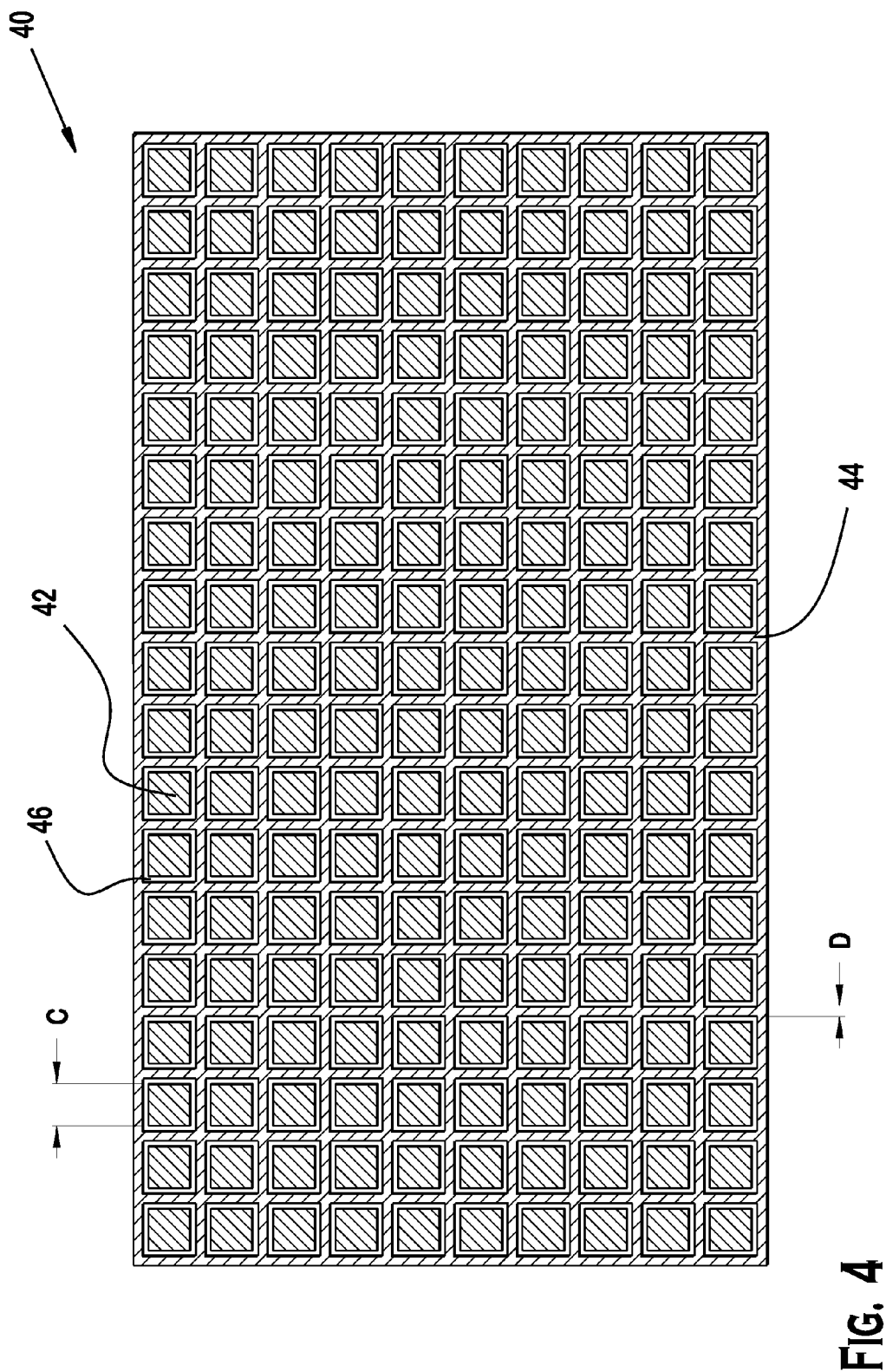
FIG. 4 is a simplified depiction of another regular square lattice array of electrochemically active areas and electrochemically inert areas of an electrode as can be employed in embodiments of the present invention.

FIG. 1 is a simplified exploded view of an electrochemical-based analytical test strip 10 according to an embodiment of the present invention. FIG. 2 is a simplified top view of electrochemical-based analytical test strip 10. FIG. 3 is a simplified depiction of a regular square lattice array 30 of electrochemically active and electrochemically inert areas of an electrode as can be employed in embodiments of the present invention. FIG. 4 is a simplified depiction of another regular square lattice array 40 of electrochemically active and electrochemically inert areas of an electrode as can be employed in embodiments of the present invention.

Referring to FIGS. 1 through 4, electrochemical-based analytical test strip 10 according to the present invention includes an electrically-insulating substrate 12, a patterned conductor layer 14, a patterned insulation layer 16, an enzymatic reagent layer 18, a patterned adhesive layer 20, a hydrophilic layer 22, and a top layer 24.

The disposition and alignment of electrically-insulating substrate 12, patterned conductor layer 14 (including reference electrode 14a, first working electrode 14b and second working electrode 14c), patterned insulation layer 16 (with electrode exposure window 17 extending therethrough), enzymatic reagent layer 18, patterned adhesive layer 20, hydrophilic layer 22 and top layer 24 of electrochemical-based analytical test strip 10 are such that sample receiving-chamber 25 is formed within electrochemical-based analytical test strip 10.

In the embodiment of FIGS. 1 and 2, patterned conductor layer 14 includes a counter electrode 14a (also referred to as a reference electrode), a first working electrode 14b, and a second working electrode 14c. Although electrochemical-based analytical test strip 10 is depicted as including three electrodes, embodiments of electrochemical-based analytical test strips, including embodiments of the present invention, can include any suitable number of electrodes.

Counter electrode 14a, first working electrode 14b and second working electrode 14c can be formed of any suitable material including, for example, gold, palladium, platinum, indium, titanium-palladium alloys and electrically conducting carbon-based materials. The formation of metal electrodes (for example gold electrodes) by conventional methods typically results in a metal electrode with a smooth, uniform and essentially entirely electrochemically active surface area. However, in embodiments of the present invention including electrochemical-based analytical test strip 10, at least one of the electrodes (for example, the first and second working electrodes 14b and 14c) has electrochemically inert areas 26 and electrochemically active areas 28 (see FIG. 2 in particular wherein the electrochemically inert areas are, for simplicity, depicted as open squares and the electrochemically active area(s) as solid lines). Moreover, the electrochemically inert areas and electrochemically active areas are of a predetermined size and a predetermined distribution such that the electrochemical response of the electrode during use of the electrochemical-based analytical test strip is essentially equivalent to a predetermined electrochemical response. Details of such electrochemically active and electrochemically inert areas are described further below with respect to FIGS. 3 and 4.

Such electrochemically inert and electrochemically active areas can be configured as a regular array including, for example, a regular square lattice array, regular rectangular array, regular triangular array, regular array of circular electrochemically inert areas, or regular array of polygons. Examples of regular square lattice arrays are depicted in FIGS. 3 and 4. Regular square lattice array 30 of FIG. 3 includes forty-five (45) electrochemically inert areas 32 and an electrically continuous electrochemically active area 34. Electrochemically inert areas 32 are configured as electrically isolated squares of 128 μm per side (dimension A in FIG. 3). The electrochemically active area 34 is configured as a lattice with a width of 10 μm (dimension B in FIG. 3). Electrochemically active area 34 is separated from each of the forty-five electrochemically inert areas by non-conductive border regions 36 created, for example, by laser ablation of an as deposited gold layer. Therefore, in the embodiment of FIG. 3, there are forty-five (45) non-conductive border regions 36. Electrochemically active area 34 is approximately 6.3% of the total geometric area of regular square lattice array 30.

Regular square lattice array 40 of FIG. 4 includes two hundred and forty (240) electrochemically inert areas 42 and an electrically continuous electrochemically active area 44. Electrochemically inert areas 42 are configured as electrically isolated squares of 48 μm per side (dimension C in FIG. 4). The electrochemically active area 44 is configured as a lattice with a width of 10 μm (dimension D in FIG. 4). Electrochemically active area 44 is separated from each of the two hundred and forty electrochemically inert areas by a non-conductive border regions 46 created, for example, by laser ablation of an as deposited gold layer. Therefore, in the embodiment of FIG. 3, there are two hundred and forty (45) non-conductive border regions 46. Electrochemically active area 44 is approximately 17.5% of the total geometric area of regular square lattice array 40.

The predetermined size and predetermined distribution of the electrochemically active and electrochemically inert areas will depend on the desired predetermined electrochemical response, whether that electrochemical response be a peak current, peak separation, transient response, early transient response, interferent response, noise response, or combination thereof. A typical, but non-limiting width of the at least one electrochemically active area is in the range of 3 μm to 50 μm while a typical but non-limiting width of the electrochemically inert areas is in the range of 20 μm to 200 μm.

Regular arrays of chemically inert areas can be formed, for example, by physical blockage of the surface of an electrode or by physically electrically isolating areas in a physical manner. Such physical isolation can be accomplished, for example, using conventional laser ablation techniques that are known to one of skill in the art. Physical blockage of the surface can be accomplished, for example, by patterned deposition of an electrically insulating material that is insoluble during use of the electrochemical-based analytical test strip. Such a patterned deposition can employ any suitable technique including, for example, an ink jet printing technique Electrically-insulating substrate 12 can be any suitable electrically-insulating substrate known to one skilled in the art including, for example, a nylon substrate, polycarbonate substrate, a polyimide substrate, a polyvinyl chloride substrate, a polyethylene substrate, a polypropylene substrate, a glycolated polyester (PETG) substrate, or a polyester substrate. The electrically-insulating substrate can have any suitable dimensions including, for example, a width dimension of about 5 mm, a length dimension of about 27 mm and a thickness dimension of about 0.5 mm.

Electrically-insulating substrate 12 provides structure to the strip for ease of handling and also serves as a base for the application (e.g., printing or deposition) of subsequent layers (e.g., a patterned conductor layer). It should be noted that patterned conductor layers employed in analytical test strips according to embodiments of the present invention can take any suitable shape and be formed of any suitable materials including, for example, metal materials and conductive carbon materials.

Patterned insulation layer 16 can be formed, for example, from a screen printable insulating ink. Such a screen printable insulating ink is commercially available from Ercon of Wareham, Mass. U.S.A. under the name "Insulayer."

Patterned adhesive layer 20 can be formed, for example, from a screen-printable pressure sensitive adhesive commercially available from Apollo Adhesives, Tamworth, Staffordshire, UK. In the embodiment of FIGS. 1-4, patterned adhesive layer 20 defines outer walls of the sample-receiving chamber 26.

Hydrophilic layer 22 can be, for example, a clear film with hydrophilic properties that promote wetting and filling of electrochemical-based analytical test strip 10 by a fluid sample (e.g., a whole blood sample). Such clear films are commercially available from, for example, 3M of Minneapolis, Minn. U.S.A.

Enzymatic reagent layer 18 can include any suitable enzymatic reagents, with the selection of enzymatic reagents being dependent on the analyte to be determined. For example, if glucose is to be determined in a blood sample, enzymatic reagent layer 18 can include oxidase or glucose dehydrogenase along with other components necessary for functional operation. Enzymatic reagent layer 18 can include, for example, glucose oxidase, tri-sodium citrate, citric acid, polyvinyl alcohol, hydroxyl ethyl cellulose, potassium ferricyanide, antifoam, cabosil, PVPVA, and water. Further details regarding enzymatic reagent layers, and electrochemical-based analytical test strips in general, are in U.S. Pat. No. 6,241,862, the contents of which are hereby fully incorporated by reference.

Details regarding the use of electrodes and enzymatic reagent layers for the determination of the concentrations of analytes in a bodily fluid sample, albeit without electrochemically active and electrochemically inert areas of predetermined size and predetermined distribution, are in U.S. Pat. No. 6,733,655, which is hereby fully incorporated by reference.

Top layer 24 includes a first portion 24a (e.g. a transparent or translucent first portion) and an opaque second portion 24b. First portion 24a and the opaque second portion 24b of the top layer are configured and aligned with the remainder of the analytical test strip such that a user can view the sample-receiving chamber through the first portion of the top layer. Top layer 24 can be, for example, a clear film, with opaque second portion 24b being created, for example, by overprinting of the clear film with an opaque ink and first portion 24a being simply clear film without overprinting. A suitable clear film is commercially available from Tape Specialities, Tring, Hertfordshire, UK.

Electrochemical-based analytical test strip 10 can be manufactured, for example, by the sequential aligned formation of patterned conductor layer 14, patterned insulation layer 16 (with electrode exposure window 17 extending therethrough), enzymatic reagent layer 18, patterned adhesive layer 20, hydrophilic layer 22 and top layer 24 onto electrically-insulating substrate 12. Any suitable techniques known to one skilled in the art can be used to accomplish such sequential aligned formation, including, for example, screen printing, photolithography, photogravure, chemical vapour deposition, sputtering, tape lamination techniques and combinations thereof.

During use of electrochemical-based analytical test strip 10 to determine an analyte concentration in a fluid sample (e.g., blood glucose concentration in a whole blood sample), electrodes 14a, 14b and 14c of patterned conductor layer 14 are employed by, for example, an associated meter to monitor an electrochemical response of the electrochemical-based analytical test strip, for example an electrochemical reaction induced current of interest. The magnitude of such a current can then be correlated with the amount of analyte present in the fluid sample under investigation. During such use, a bodily fluid sample is introduced into sample-receiving chamber 25 of electrochemical-based analytical test strip 10.

Figure 5:
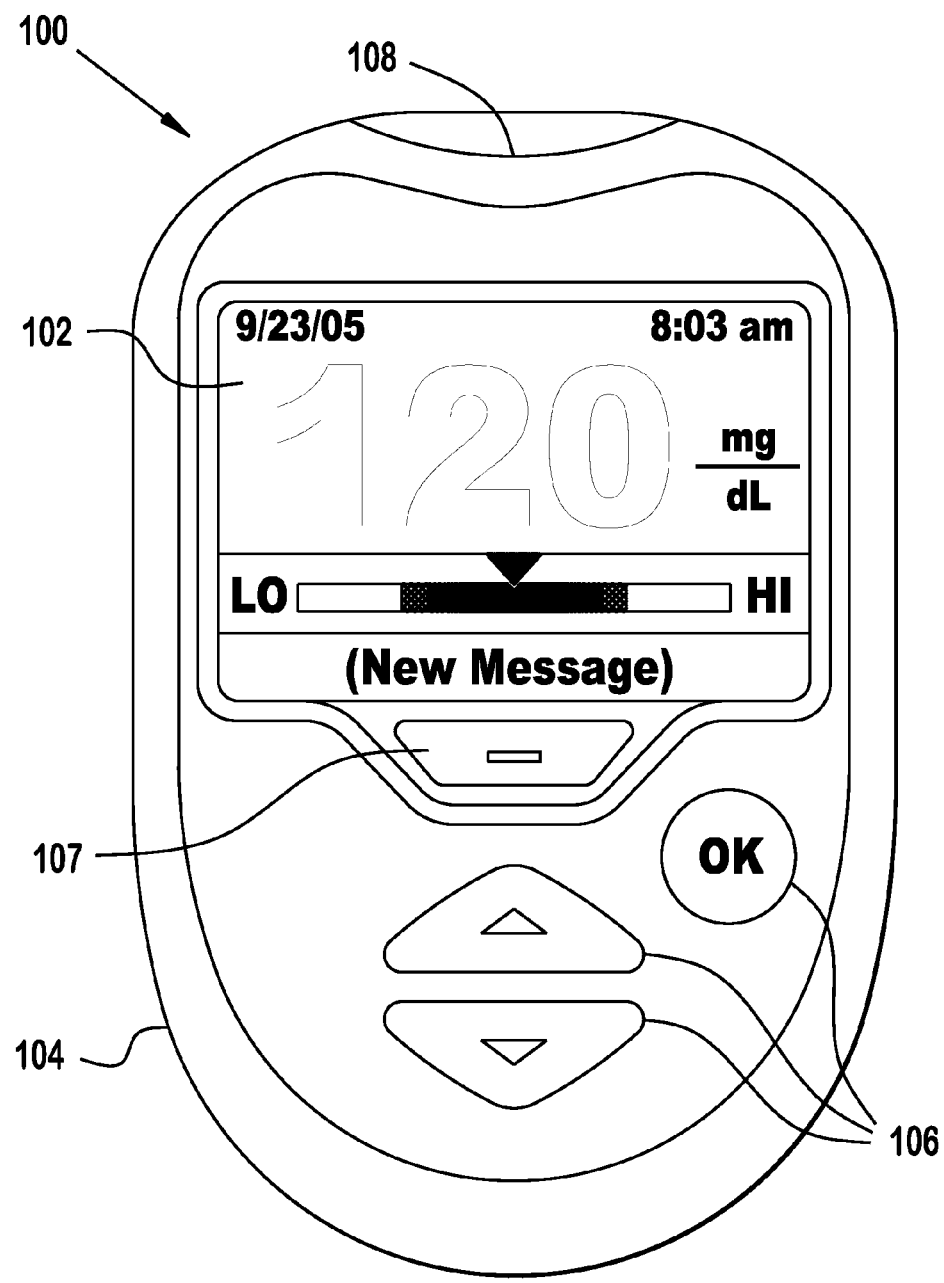
FIG. 5 is a simplified depiction of an associated meter for use in combination with electrochemical-based analytical test strips according to embodiments of the present invention.
Figure 6:
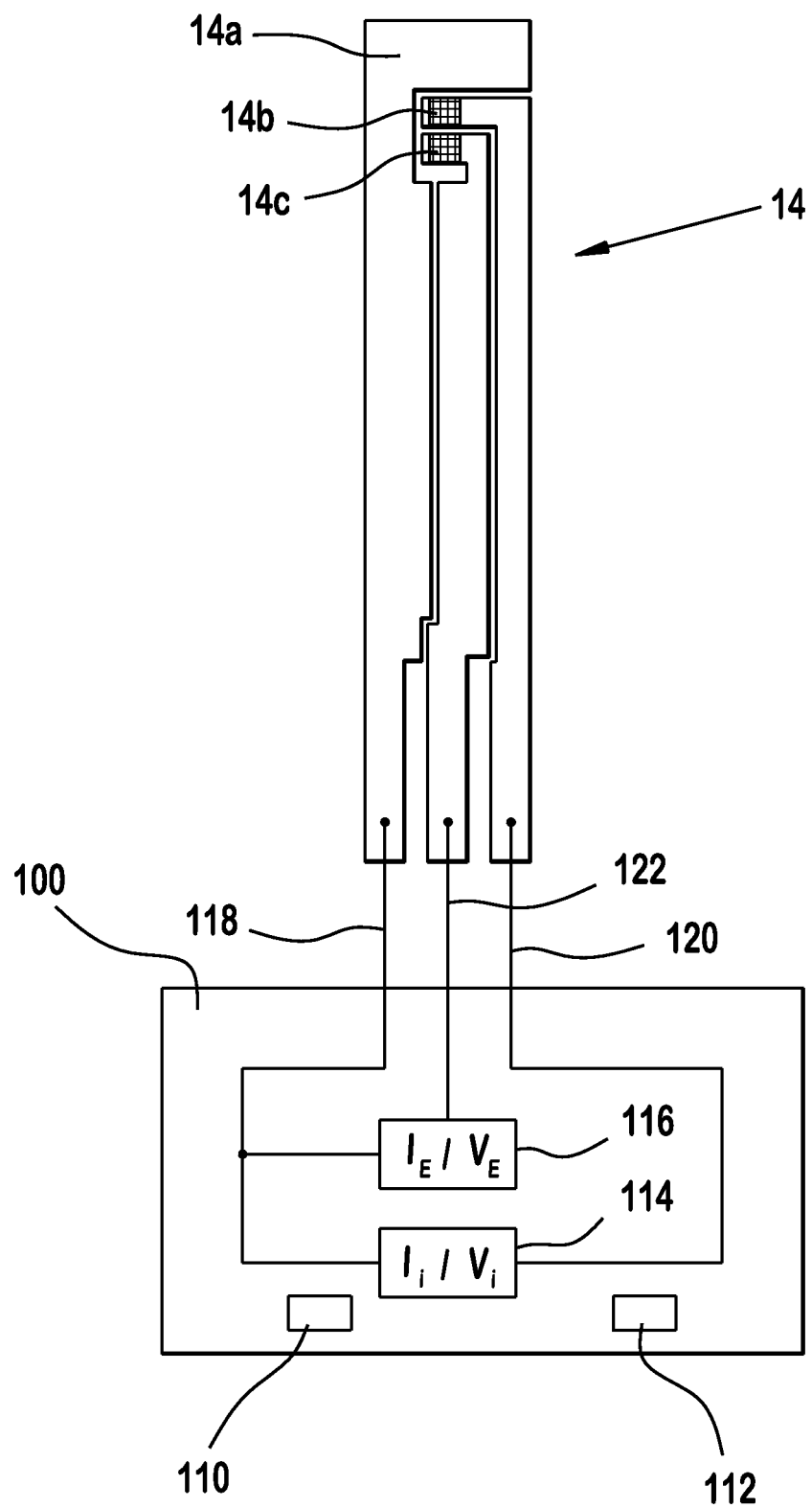
FIG. 6 is a simplified top view, schematic and block diagram illustrating a patterned conductor layer of an electrochemical-based analytical test strip according to the present invention interfaced with the associated meter of FIG. 5.

FIG. 5 is a simplified depiction of a meter 100 for use in combination with electrochemical-based analytical test strips according to embodiments of the present invention (also referred to as an "associated meter"). FIG. 6 is a simplified top view and block diagram illustrating patterned conductor layer 14 of electrochemical-based analytical test strip 10 interfacing with an associated meter 100.

Meter 100 includes a display 102, a housing 104, a plurality of user interface buttons 106, an optional soft key 107 and a strip port connector 108. Meter 100 further includes electronic circuitry within housing 104 such as a memory 110, a microprocessor 112, electronic components 114 and 116 for applying a test voltage, and also for measuring a plurality of test current values. Electrochemical-based analytical test strip 10 is configured for operative insertion into strip port connector 108.

Memory 110 of meter 100 includes a suitable algorithm that determines an analyte based on the electrochemical response of electrochemical-based analytical test strip 10. The algorithm, therefore, accommodates the electrochemical response of the electrodes within electrochemical-based analytical test strip 10.

Meter 100 also includes a reference electrode connector 118, a first working electrode connector 120 and a second working electrode connector 122. The three aforementioned connectors are part of strip port connector 108. When performing a test, a first test voltage source 114 may apply a plurality of test voltages $V_i$ between first working electrode 14b and reference electrode 14a, wherein i ranges from 1 to n and more typically 1 to 5. As a result of the plurality of test voltages $V_i$, meter 100 may then measure a plurality of test currents $I_i$. In a similar manner, second test voltage source 116 may apply a test voltage $V_E$ between second working electrode 14c and reference electrode 14a. As a result of the test voltage $V_E$, meter 100 may then measure a test current $I_E$. Test voltages $V_i$ and $V_E$ may be applied to first and second working electrodes, respectively, either sequentially or simultaneously. Those skilled in the art will recognize that the working electrode to which $V_i$ and $V_E$ are applied may be switched, i.e., that $V_i$ may be applied to second working electrode and $V_E$ may be applied to first working electrode.

As previously mentioned, the selection of predetermined size and predetermined distribution for the electrochemically inert areas and at least one electrochemically active area of electrode(s) employed in electrochemical-based analytical test strips according to the present invention can be based on the use of voltammetric sizing to estimate surface blockage (i.e., the size of electrochemically inert areas).

It has been determine that the diffusion characteristics of heterogeneous electrodes, and consequently the current response obtained during an electrochemical measurement, are determined largely by the size and distribution of electrochemically inert areas. There are essentially five scenarios of interest with respect to employing voltammetric sizing: (1) a completely unblocked electrode wherein the electrochemical response can be theoretically predicted by one skilled in the art (e.g., with the Randles Sevcik equation); (2) relatively large electrochemically active area(s) with insignificant edge effects and linear diffusion; (3) electrochemically active areas of relatively small dimensions (such as a relatively small width) with dominant edge effects and non-linear/radial diffusion; (4) electrochemically active area(s) of relatively small dimensions with dominant edge effects and partially overlapping non-linear/radial diffusion; and (5) electrochemically active area(s) of relatively small dimensions that are sufficiently close to one another that their diffusion layers completely overlap.

For scenario 1, the peak current and peak separation are as predicted by conventional theory. For scenario 2, the peak current is directly proportional to the electrode geometric area and the peak separation is as predicted by conventional theory. For scenario 3, there is no peak current but simply a steady state limiting current. For scenario 4, the peak current is lower than theory and the peak separation is greater than theory. For scenario 5, the peak current is as predicted by theory and the peak separation is greater than theory.

The observations above with respect to the five scenarios enable voltammetric sizing (measurement) of blockage size on an electrode by employing a range of scan rates and solution concentrations, diffusion layer thickness can be varied and the peak current and peak separation as a function of diffusion layer thickness measured.

Figure 7:
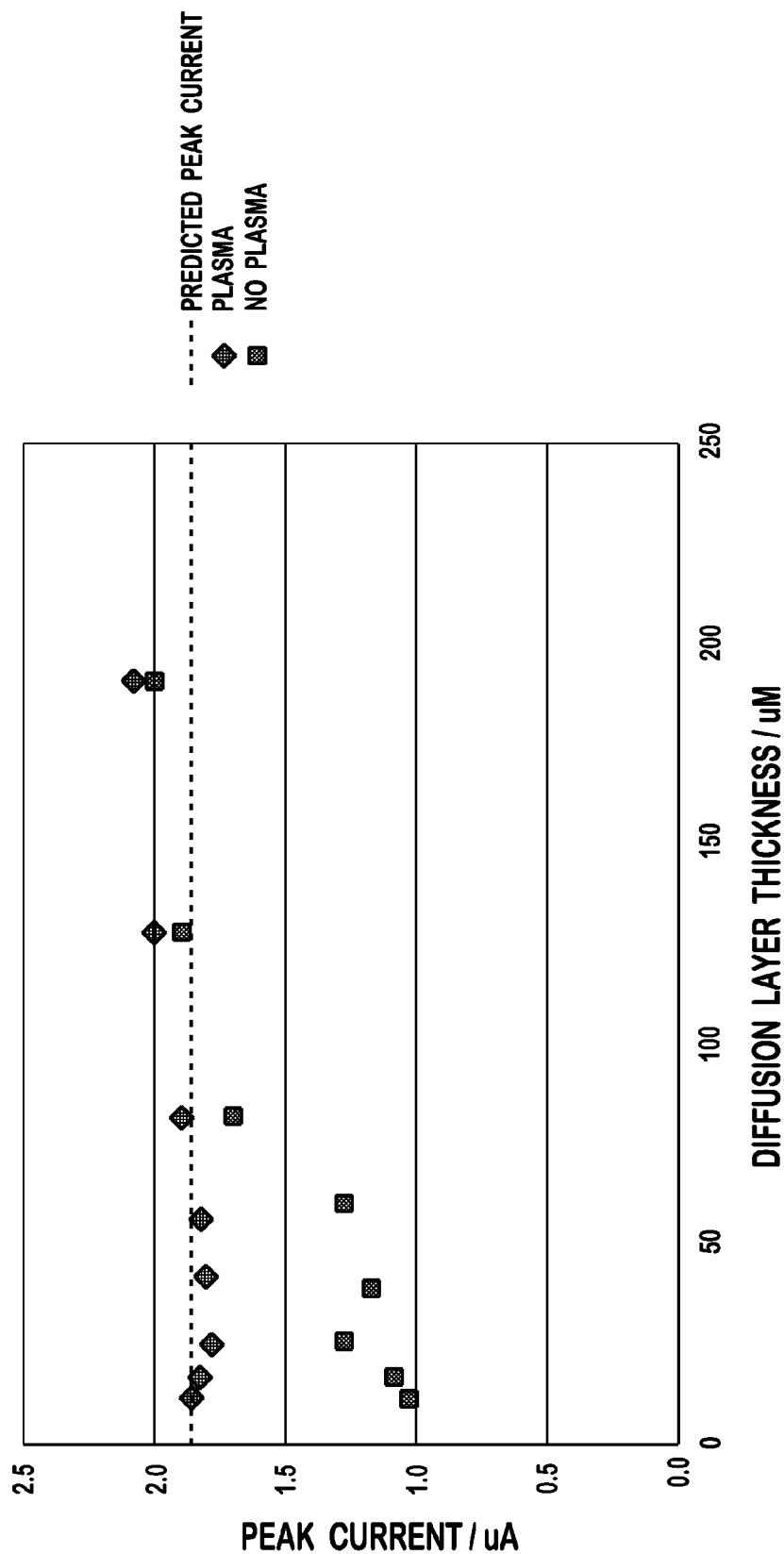
FIG. 7 is a graph depicting an example of the dependence of peak current on diffusion layer thickness for reduction of ruthenium hexamine chloride in 1M KCl at untreated (i.e., no plasma) and plasma-treated screen printed carbon electrodes in comparison to a theoretically predicted peak current.
Figure 8:
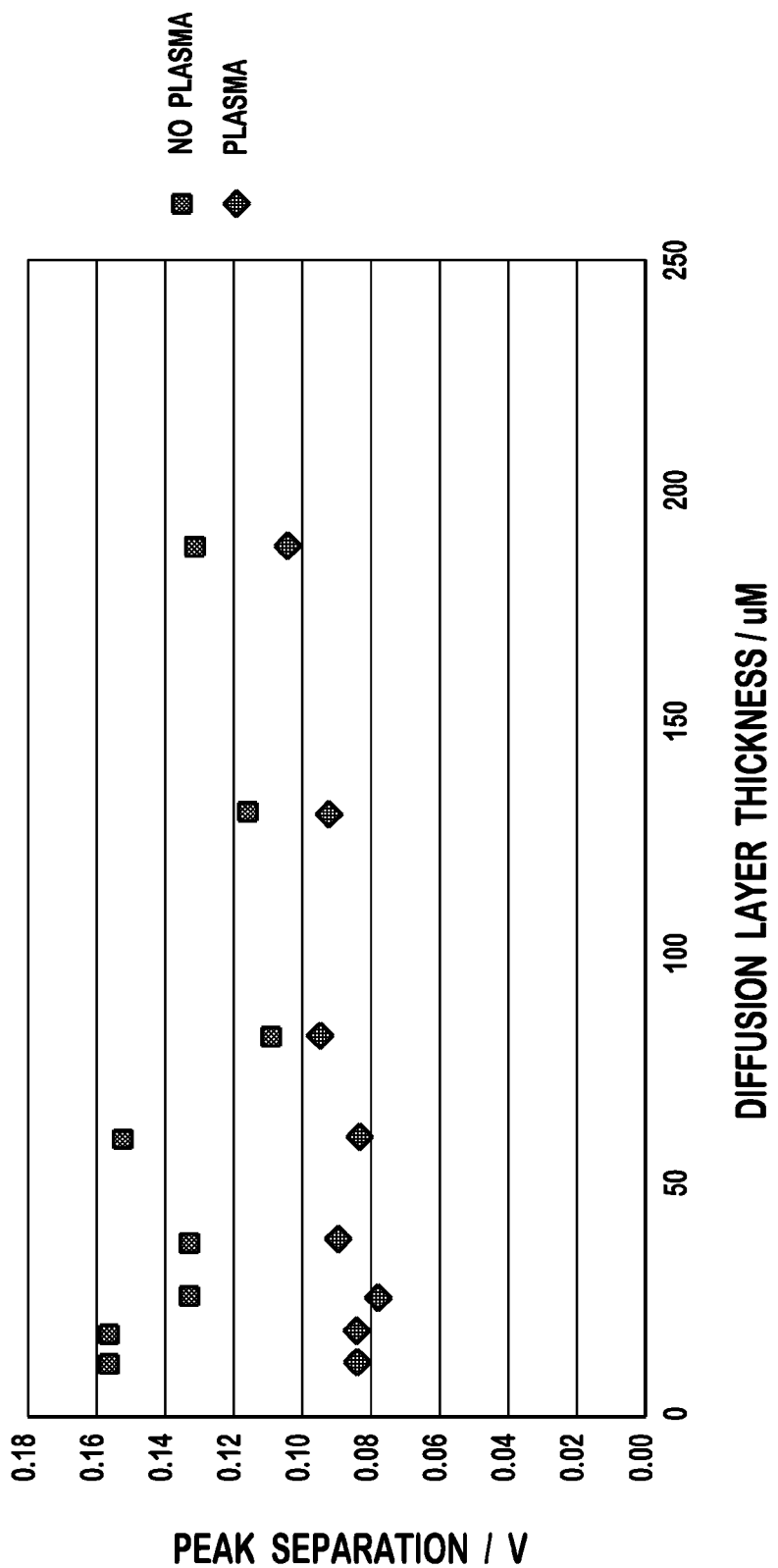
FIG. 8 is a graph depicting an example of the dependence of peak separation on diffusion layer thickness for reduction of ruthenium hexamine chloride in 1M KCl at untreated (i.e., no plasma) and plasma-treated screen printed carbon electrodes.
Figure 9:
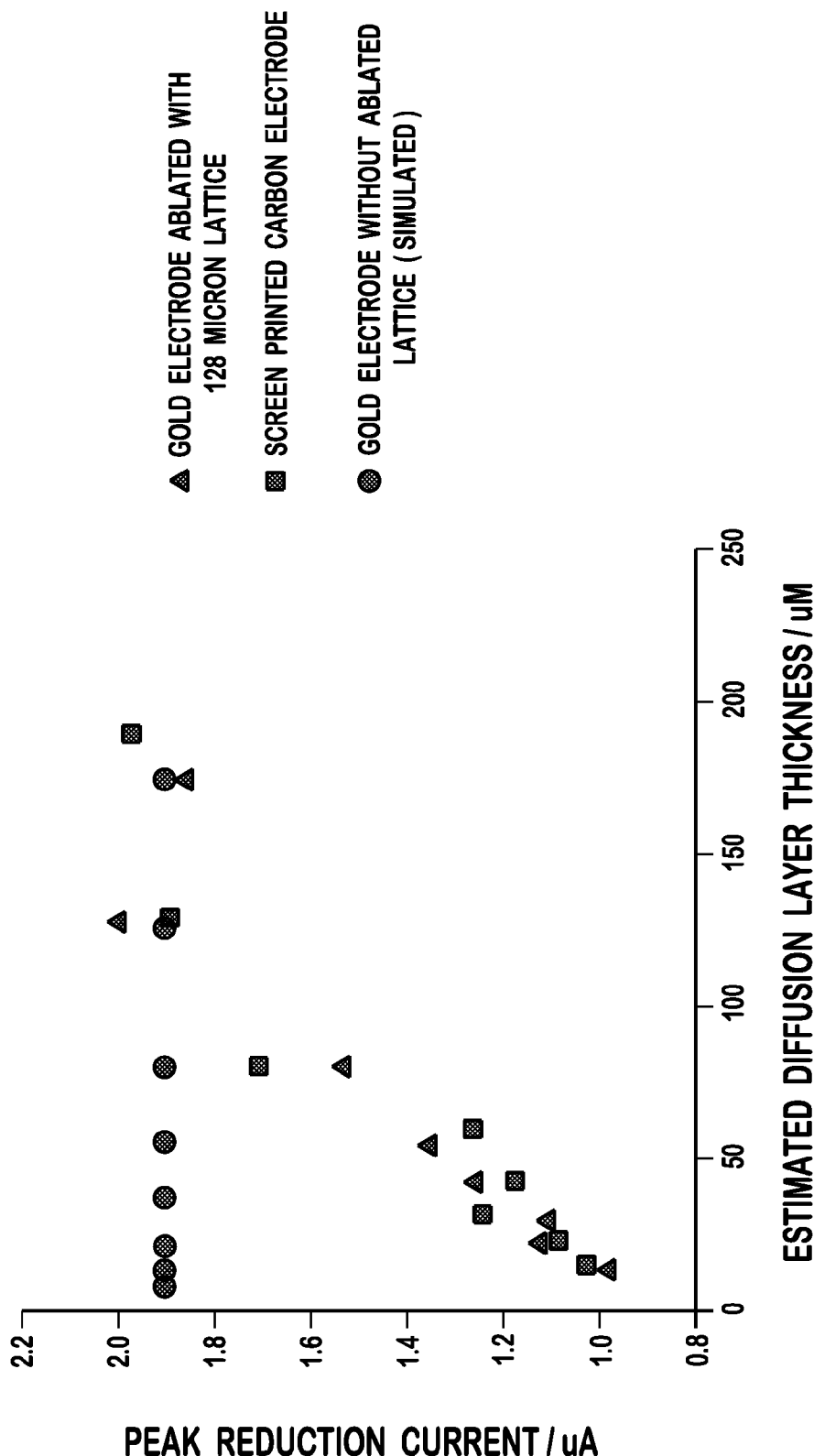
FIG. 9 is a graph depicting experimental results of a voltammetric sizing analysis of screen printed carbon, a simulated gold electrode, and a gold electrode with a 128 micron regular lattice of electrochemically active and electrochemically inert areas created via laser ablation of a deposited gold electrode.

FIG. 7 is a graph depicting an example of the dependence of peak current on diffusion layer thickness for reduction of ruthenium hexamine chloride in 1M KCl at untreated (i.e., no plasma treatment) and plasma-treated screen printed carbon electrodes in comparison to a theoretically predicted peak current. FIG. 8 is a graph depicting an example of the dependence of peak separation on diffusion layer thickness for reduction of ruthenium hexamine chloride in 1M KCl at untreated (i.e., no plasma treatment) and plasma-treated screen printed carbon electrodes. FIG. 9 is a graph depicting experimental results of a voltammetric sizing analysis of screen printed carbon, a simulated gold electrode, and a gold electrode (approximately 35 nm in thickness and produced via sputtering) with a 128 micron regular lattice of electrochemically active and electrochemically inert areas (see FIG. 3) created via laser ablation of a deposited gold electrode. The data of FIGS. 7-9 was obtained using a working electrode of 0.0056 cm$^2$, a 3 electrode configuration with Pt coil counter electrode, Ag/AgCl reference electrode, potential scan rates from 10 to 2000 mV/s and the Ruthenium Hexamine concentration reduced from 4.44 mM to 0.31 mM as the potential scan rate increased such that predicted peak current was 1.87 μA in all measurements.

FIG. 7 indicates that screen printed carbon electrodes (without plasma treatment) deviate from the predicted peak current at a diffusion layer thickness of around 75 μm. Similarly, FIG. 8 indicates that the peak separation of the plasma treated and non-plasma treated electrodes deviate from one another at diffusion layer thicknesses of less that approximately 75 μm. These two results indicate that screen printed carbon electrodes without plasma treatment have a characteristic surface blockage dimension (i.e., electrochemically inert area characteristic width) of 75 μm.

A gold electrode with the regular square lattice array of FIG. 3 was created in order to demonstrate that the electrochemical response of such a gold electrode would be essentially equivalent to a predetermined electrochemical response (i.e., the electrochemical response of a screen printed carbon electrode). FIG. 9 depicts the results of the voltammetric sizing and indicates that the peak reduction current of the gold electrode with predetermined electrochemically active and predetermined electrochemically inert areas does indeed provide an electrochemical response essentially equivalent to the predetermined response (i.e., the response of a screen printed carbon electrode). FIG. 9 also indicates that a conventional gold electrode would not provide an electrochemical response that was equivalent to that of a screen printed carbon electrode.

It is hypothesized without being bound, that during the transient response at electrodes with electrochemically inert areas and at least one electrochemically active area of the appropriate predetermined size and predetermined distribution as described herein, transitions from scenario 3 through scenario 5 would occur and that the relative magnitudes of analyte, interferent and noise signals would vary between these scenarios. In this situation, employing a plurality of electrodes, each with a different predetermined size and predetermined distribution of electrochemically inert areas and at least one electrochemically active area, the magnitude of the analyte, interferent and noise signals could be staggered in time. A suitable algorithm could then be employed to deconvolute the analyte, interferent and noise signals an produce an analyte determination of improved accuracy in comparison to conventional electrodes.

Referring to FIGS. 1, 5 and 6 in particular, an electrochemical-based analytical test strip and associated meter for the determination of an analyte (e.g., glucose) in a bodily fluid sample (such as a whole blood sample) includes an electrochemical-based analytical test strip (such as electrochemical-based analytical test strip 10 described above) having an electrically insulating base layer and a patterned conductor layer (for example, a gold patterned conductor layer) disposed over the electrically-insulating layer. The patterned conductor layer includes at least one electrode with the electrode having electrochemically inert areas and at least one electrochemically active area. Moreover, the electrochemically inert areas and electrochemically active area(s) are of a predetermined size and a predetermined distribution such that the electrochemical response of the electrode during use of the electrochemical-based analytical test strip is essentially equivalent to a predetermined electrochemical response.

Also included is a meter (for example, meter 100 described above and depicted in FIGS. 5 and 6) with an algorithm, the meter and algorithm being configured to determine an analyte in a bodily fluid sample applied to the electrochemical-based analytical test strip based on the electrochemical response of the electrode.

Once apprised of the present disclosure, one skilled in the art will recognize that embodiments according to the present invention that are a combination of an electrochemical analytical test strip and associated meter can incorporate any of the techniques, benefits and characteristics of electrochemical-based analytical test strips according to embodiments of the present invention and described herein. Such combinations can be thought of as a kit or assemblage.

Figure 10:
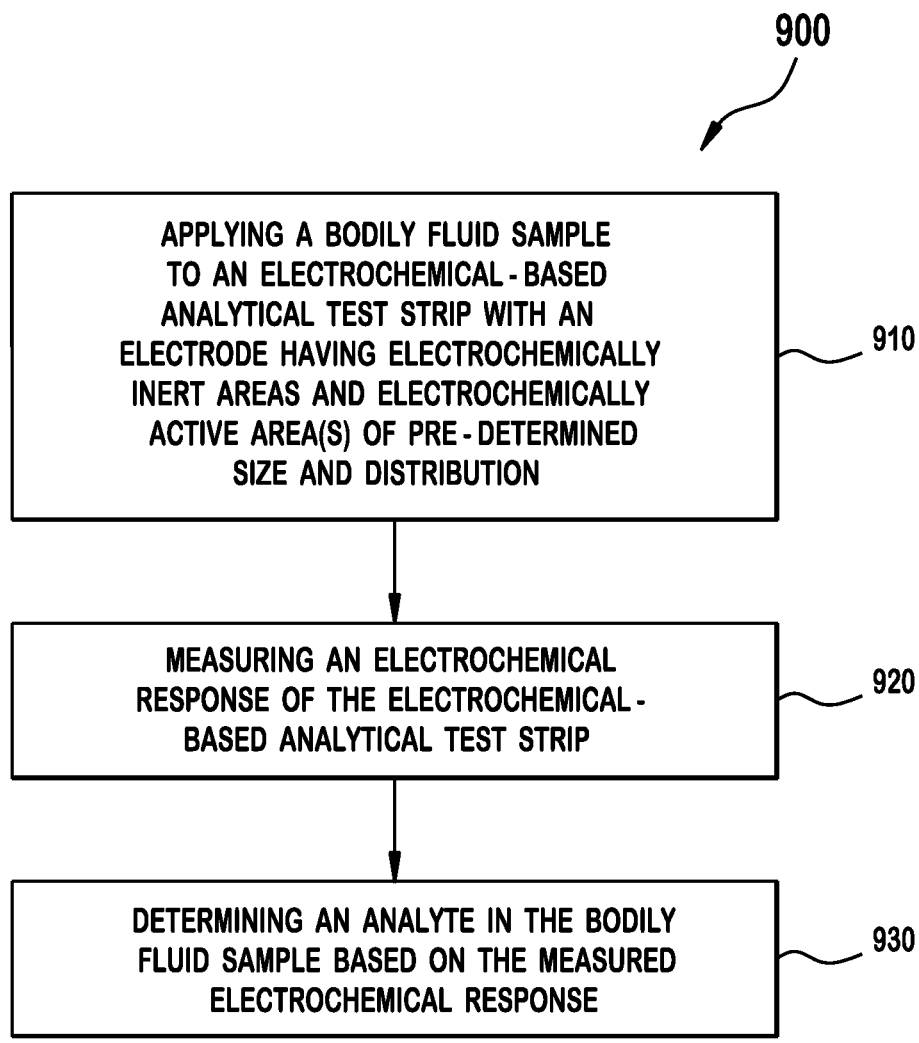
FIG. 10 is a flow diagram depicting stages in a method for determining an analyte in a bodily fluid sample according to an embodiment of the present invention.

Referring to FIG. 10, a method 900 for determining an analyte (such as glucose) in a bodily fluid sample includes applying a bodily fluid sample (for example, a whole blood bodily fluid sample) to an electrochemical-based analytical test strip having an electrically insulating base layer and a patterned conductor layer (for example, a gold patterned conductor layer) disposed over the electrically-insulating layer (see step 910 of FIG. 9). The patterned conductor layer of step 910 includes at least one electrode with electrochemically inert areas and electrochemically active area(s) (i.e., a heterogeneous electrode). Moreover, the electrochemically inert areas and electrochemically active area(s) are of a predetermined size and a predetermined distribution such that electrochemical response of the electrode during use of the electrochemical-based analytical test strip is essentially equivalent to a predetermined electrochemical response.

At step 920, the method includes measuring an electrochemical response of the electrochemical-based analytical test strip and, at step 930, determining the analyte based on the measured electrochemical response. Once apprised of the present disclosure, one skilled in the art will recognize that method 900 can be readily modified to incorporate any of the techniques, benefits and characteristics of analyte test strips according to embodiments of the present invention and described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

What is claimed is:

1. An electrochemical-based analytical test strip for the determination of an analyte in a bodily fluid sample, the electrochemical-based analytical test strip comprising:
an electrically insulating base layer; and
a patterned conductor layer disposed over the electrically-insulating layer, the patterned conductor layer including at least one electrode,
wherein the at least one electrode has electrochemically inert areas, an electrically continuous electrochemically active area lattice, and non-conductive border regions separating the electrochemically inert areas and the electrically continuous electrochemically active area lattice, the electrochemically inert areas and the at least one electrochemically active area being of a predetermined size and a predetermined distribution such that electrochemical response of the electrode during use of the electrochemical-based analytical test strip is essentially equivalent to a predetermined electrochemical response of a different electrode.

2. The electrochemical-based analytical test strip of claim 1 wherein the patterned conductor layer is a gold patterned conductor layer and the at least one electrode is a working electrode.

3. The electrochemical-based analytical test strip of claim 1 wherein the electrochemically inert areas are rendered electrochemically inert via physical electrical isolation from the electrically continuous electrochemically active area lattice.

4. The electrochemical-based analytical test strip of claim 3 wherein the physical electrical isolation is achieved using laser ablation.

5. The electrochemical-based analytical test strip of claim 1 wherein the electrochemically inert areas and electrically continuous electrochemically active area lattice of a predetermined size and a predetermined distribution are configured in a regular array.

6. The electrochemical-based analytical test strip of claim 5 wherein the regular array is a regular square lattice array.

7. The electrochemical-based analytical test strip of claim 6 wherein a width of the electrically continuous electrochemically active area lattice is in the range of 3 μm to 50 μm.

8. The electrochemical-based analytical test strip of claim 6 wherein the width of the electrochemically inert areas is in the range of 20 μm to 200 μm.

9. The electrochemical-based analytical test strip of claim 1 wherein the analytical test strip is configured for the determination of glucose in a whole blood sample.

10. The electrochemical-based analytical test strip of claim 1 wherein the patterned conductor layer has a first working electrode, a second working electrode and a counter/reference electrode and wherein each of the first working electrode and the second working electrode have electrochemically inert areas and an electrically continuous electrochemically active area lattice, the electrochemically inert areas and electrically continuous electrochemically active area lattice being of a predetermined size and a predetermined distribution such that an electrochemical response of the electrode during use of the electrochemical-based analytical test strip is essentially equivalent to a predetermined electrochemical response of a screen-printed carbon electrode.

11. The electrochemical-based analytical test strip of claim 1 wherein the predetermined electrical response is a peak current response.

12. The electrochemical-based analytical test strip of claim 1 wherein the predetermined electrical response is a peak separation response.

13. The electrochemical-based analytical test strip of claim 1 wherein the predetermined electrical response is an early transient response occurring within approximately 500 milliseconds of a potential application to the electrochemical-based analytical test strip.

14. The electrochemical-based analytical test strip of claim 1 wherein the predetermined electrical response is an interferent sensitivity response.

15. The electrochemical-based analytical test strip of claim 1 further including:
an enzymatic reagent layer disposed at least over at least a portion of the patterned conductor layer;
a top layer disposed over the enzymatic reagent layer; and
a sample receiving chamber defined within the electrochemical-based analytical test strip.

16. The electrochemical-based analytical test strip of claim 1 wherein the patterned conductor layer includes a plurality of electrodes, each of the plurality of electrodes having a different predetermined size and predetermined distribution of electrochemically inert areas and electrically continuous electrochemically active area lattice.

17. An electrochemical-based analytical test strip and associated meter for the determination of an analyte in a bodily fluid sample, the electrochemical-based analytical test strip and associated meter comprising:
   an electrochemical-based analytical test strip having:
      an electrically insulating base layer; and
      a patterned conductor layer disposed over the electrically-insulating layer, the patterned conductor layer including at least one electrode; wherein the at least one electrode has electrochemically inert areas, an electrically continuous electrochemically active area lattice, and non-conductive border regions separating the electrochemically inert areas and the electrically continuous electrochemically active area lattice, the electrochemically inert areas and electrically continuous electrochemically active area lattice being of a predetermined size and a predetermined distribution such that electrochemical response of the electrode during use of the electrochemical-based analytical test strip is essentially equivalent to a predetermined electrochemical response of a screen-printed carbon electrode; and
   a meter that includes an algorithm, the meter and algorithm configured to determine an analyte in a bodily fluid sample applied to the electrochemical-based analytical test strip based on the electrochemical response of the electrode.

18. The electrochemical-based analytical test strip and associated meter of claim 17 wherein the electrode is a gold electrode.

19. The electrochemical-based analytical test strip and meter of claim 17 wherein the electrochemically inert areas are rendered electrochemically inert via physical electrical isolation from the electrically continuous electrochemically active area lattice.

20. The electrochemical-based analytical test strip and meter of claim 19 wherein the physical electrical isolation is achieved using laser ablation.

21. The electrochemical-based analytical test strip and meter of claim 17 wherein the electrochemically inert areas and electrically continuous electrochemically active area lattice of a predetermined size and a predetermined distribution are configured in a regular array.

22. The electrochemical-based analytical test strip and meter of claim 20 wherein the regular array is a regular square lattice array.

23. The electrochemical-based analytical test strip and meter of claim 21 wherein a width of the electrically continuous electrochemically active area lattice is in the range of 3 µm to 50 µm.

24. The electrochemical-based analytical test strip and meter of claim 21 wherein the width of the electrochemically inert areas is in the range of 20 µm to 200 µm.

25. The electrochemical-based analytical test strip and meter of claim 17 wherein the analytical test strip is configured for the determination of glucose in a whole blood sample.

26. The electrochemical-based analytical test strip and meter of claim 17 wherein the predetermined electrical response is a peak current response.

27. The electrochemical-based analytical test strip and meter of claim 17 wherein the predetermined electrical response is a peak separation response.

28. The electrochemical-based analytical test strip and meter of claim 17 wherein the predetermined electrical response is an early transient response.

29. The electrochemical-based analytical test strip and meter of claim 17 wherein the predetermined electrical response is an interferent sensitivity response.

30. The electrochemical-based analytical test strip and meter of claim 17 wherein the patterned conductor layer includes a plurality of electrodes, each of the plurality of electrodes having a different predetermined size and predetermined distribution of electrochemically inert areas and an electrochemically active area lattice.

* * * * *

UNITED STATES PATENT AND TRADEMARK OFFICE
CERTIFICATE OF CORRECTION

PATENT NO.       : 8,940,141 B2
APPLICATION NO.  : 12/783437
DATED            : January 27, 2015
INVENTOR(S)      : Macfie et al.

Page 1 of 1

It is certified that error appears in the above-identified patent and that said Letters Patent is hereby corrected as shown below:

In the claims

Claim 1, column 10, line 3, delete "different electrode" and insert --screen-printed carbon electrode--.

Signed and Sealed this
Fifteenth Day of December, 2015

Michelle K. Lee
*Director of the United States Patent and Trademark Office*